(12) United States Patent
Ringold et al.

(10) Patent No.: US 8,354,244 B2
(45) Date of Patent: *Jan. 15, 2013

(54) METHOD FOR DIAGNOSING HEMANGIOSARCOMA IN CANINE USING DETECTION OF THYMIDINE KINASE ACTIVITY

(76) Inventors: Randy Ringold, West Hills, CA (US); Renee Parker, Woodbury, MN (US); Douglas H Thamm, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/323,670

(22) Filed: Dec. 12, 2011

(65) Prior Publication Data

US 2012/0156690 A1 Jun. 21, 2012

Related U.S. Application Data

(63) Continuation of application No. 12/260,885, filed on Oct. 29, 2008, now Pat. No. 8,097,432.

(60) Provisional application No. 60/983,359, filed on Oct. 29, 2007.

(51) Int. Cl.
*C12Q 1/48* (2006.01)
(52) U.S. Cl. .......................................................... 435/15
(58) Field of Classification Search ...................... 435/15
See application file for complete search history.

(56) References Cited

U.S. PATENT DOCUMENTS

| 8,097,432 B2 * | 1/2012 | Ringold et al. ................. 435/15 |
| 2006/0035295 A1 | 2/2006 | Oehrvik et al. |
| 2006/0100286 A1 | 5/2006 | Cohen et al. |

FOREIGN PATENT DOCUMENTS

| WO | WO 2006/031524 | 3/2006 |
| WO | PCT/US2008/081630 | 5/2009 |

OTHER PUBLICATIONS

"Clinical Significance of Serum Thymidine Kinase in Adult T-Cell Leukemia and Acute Myeloid Leukemia" Sadamori et al., British Journal of Haematology, vol. 90, pp. 100-105, 1995.
"Serum Thymidine Kinase in Non-Hodgkin Lymphomas with Special Regard to Multiple Myeloma" Poley et al., Anticancer Research, vol. 17, pp. 3025-3030, 1997.
"Serum Thymidine Kinase Activity in Dogs with Malignant Lymphoma: A Potent Marker for Prognosis and Monitoring the Disease" J. Vet. Intern Med. vol. 18, pp. 696-702, 2004.
"Elevated Serum Thymidine Kinase Levels Identify a Subgroup at High Risk of Disease Progression in Early, Nonsmoldering Chronic Lymphocytic Leukemia" Hallek et al., Blood, vol. 93, No. 5, pp. 1732-1737, Mar. 1, 1999.
"A Non-radiometric Method for Measuring Serum Thymidine Kinase Activity in Malignant Lymphoma in dogs" Von Euler et al. Research in Veterinary Science, vol. 80, pp. 17-24, 2006.
"Thymidine Kinase: a tumor marker with prognostic value for non-Hodgkin's lymphoma and a broad range of potential clinical applications" Hallek et al. Ann Hematol. vol. 65, pp. 1-5, 1992.
"Thymidine phosphorylase expression in Kaposi sarcoma" Dada et al., J. Clin. Pathol. vol. 49, pp. 400-402, 1996.

* cited by examiner

*Primary Examiner* — Ralph Gitomer
(74) *Attorney, Agent, or Firm* — Karim Lagobi

(57) ABSTRACT

The disclosure relates to a method for detecting hemangiosarcoma in canines. The method includes the steps of: (1) obtaining a quantity of blood from the subject canine; (2) separating the quantity of blood into a serum portion and a non-serum portion; (3) contacting the serum portion of the blood with a detector to detect presence of an amount of Thymidine Kinase (TK); and (4) detecting the level of TK in serum and determining whether TK is present in amounts of about 8 units/L or greater.

7 Claims, 3 Drawing Sheets

TABLE 1 - CANCER (TK) STUDY RESULTS

ASSAY RANGE 0.5-100
ANALYTICAL SENSITIVITY <0.5
FUNCTIONAL SENSITIVITY <5

| DATABASE CODE | DATE OF BIRTH | SPECIES | BREED | SEX | HISTOLOGY | Topo+vet | TUMOR LOCATION | SAMPLE TYPE | SAMPLE AMOUNT | PROCESS TIME | MEAN | Conc.CV | HEMOLYZ ED(1-4) |
|---|---|---|---|---|---|---|---|---|---|---|---|---|---|
| 68770 | 07/26/95 | CANINE | GERMAN SHEPHERD | MN | BC-HSA | - | SPLENIC, HEPATIC, OM | SERUM | - | - | 17.7 | 2.3 | ++ |
| 33363 | 01/01/95 | CANINE | GERMAN SHEPHERD | MN | BC-HSA | - | | SERUM | - | - | 13.7 | 2.0 | |
| 71809 | 12/31/94 | CANINE | GERMAN SHORTHAIR POINTER | MN | BC-HSA | - | SPLENIC | SERUM | - | - | 1.2 | 2.1 | |
| 71914 | 06/27/93 | CANINE | LABRADOR | FS | BC-HSA | - | SPLENIC & HEPATIC | SERUM | - | - | 1.2 | 0.6 | ++ |
| 64345 | 08/31/97 | CANINE | LAB RET | MN | BC-HSA | - | SPLENIC & HEPATIC | SERUM | - | - | >100 | | ++ |
| 73361 | 05/15/94 | CANINE | SHEP X | FS | BC-HSA | - | | SERUM | - | - | 13.3 | 0.3 | |
| 77912 | 02/14/95 | CANINE | GERMAN SHEPHERD | MN | BC-HSA | - | | SERUM | - | - | >100 | | |
| 81605 | 05/27/98 | CANINE | LAB X | MN | BC-HSA | - | SPLENIC | SERUM | - | - | 3.1 | 1.9 | |
| 81063 | 08/22/92 | CANINE | GERMAN SHEPHERD | MN | BC-HSA | - | | SERUM | - | - | 41.4 | 3.1 | |
| 74520 | 03/14/91 | CANINE | BORDER COLLIE X | FS | Nec-HSA | - | | SERUM | - | - | 42.7 | 1.6 | |
| 26737 | 02/20/99 | CANINE | BORDER COLLIE | MN | Nec-HSA | - | | SERUM | - | - | 0.1 | | |
| 80869 | 02/05/95 | CANINE | IRISH SETTER | MN | Nec-HSA | - | | SERUM | - | - | >100 | | |
| 51883.2 | 10/10/94 | CANINE | SHEP X | MN | Nec-HSA | - | | SERUM | - | - | 8.7 | 1.6 | +++ |
| 69554 | 03/31/92 | CANINE | SHEP X | MN | Nec-HSA | - | | SERUM | - | - | 8.0 | 50.3 | |
| 81380 | 12/05/95 | CANINE | GERMAN SHEPHERD | MN | Nec-HSA | - | | SERUM | - | - | 9.5 | 1.2 | |
| 76679 | 11/04/94 | CANINE | COCKAPOO | FS | Nec-HSA | - | | SERUM | - | - | 58.9 | 1.0 | |
| 71372 | 10/17/91 | CANINE | RET/LAB X | FS | Nec-HSA | - | | SERUM | - | - | 40.6 | 2.1 | + |
| 20514.02 | 10/21/91 | CANINE | BOXER | MN | Nec-HSA | - | | SERUM | - | - | 3.1 | 1.1 | + |
| 73450 | 06/01/91 | CANINE | SPRINGER SPANIEL | MN | Nec-HSA | - | | SERUM | - | - | 11.5 | 8.8 | |
| 73415 | 12/28/94 | CANINE | GOLDEN RETRIEVER | MN | Nec-HSA | - | | SERUM | - | - | 16.4 | 1.0 | |

Fig. 1

TABLE 2A - CONTROL SAMPLE

| SEX | AGE(YR) | ID | RUN 1 | RUN 2 | RUN 3 | MEAN | CONC CV |
|---|---|---|---|---|---|---|---|
| M | 8 | A | 3.8 | 3.5 | 3.7 | 3.7 | 5 |
| F | 12 | B | 5.7 | 5.7 | 5.4 | 5.6 | 2.3 |
| M | 15 | C | 1.7 | 1.7 | 1.7 | 1.7 | 1 |
| M | 8 | D | 3.7 | 3.8 | 3.6 | 3.7 | 3.1 |
| M | 6 | E | 1.5 | 1.4 | 1.4 | 1.4 | 5.9 |
| F | 11 | F | 2.1 | 1.9 | 2 | 2 | 3.3 |
| M | 12 | G | 1.6 | 1.4 | 1.5 | 1.5 | 7.3 |
| M | 12 | H | 1.4 | 1.3 | 1.5 | 1.4 | 4.9 |
| F | 8 | I | 2.3 | 2.1 | 2 | 2.1 | 7 |
| M | 8 | J | 4.2 | 4 | 4 | 4.1 | 3.7 |
| M | 13 | K | 1.5 | 1.6 | 1.6 | 1.6 | 3.3 |
| M | 8 | L | 3.1 | 3.1 | 3.1 | 3.1 | 1.6 |
| F | 4 | Ab | 4.5 | 4.4 | 4.4 | 4.4 | 1.3 |

Fig. 2A

TABLE 2B - CONTROL SAMPLE

| SEX | AGE(YR) | ID | RUN 1 | RUN 2 | RUN 3 | MEAN | CONC CV |
|---|---|---|---|---|---|---|---|
| F | 7 | 1 | 1 | 0.9 | 1 | 1 | 7.5 |
| F | 10 | 2 | 3.9 | 3.7 | 3.8 | 3.8 | 3 |
| M | 15 | 3 | 5.5 | 5.2 | 5.3 | 5.3 | 2.8 |
| M | 7 | 4 | 0.1 | <0 | 0 | 0 | |
| F | 11 | 5 | 3.7 | 3.7 | 3.8 | 3.8 | 2.1 |
| F | 7 | 6 | 2.3 | 1.7 | 1.7 | 1.9 | 17.6 |
| F | 12 | 7 | 1.2 | 1.2 | 1.2 | 1.2 | 2.1 |
| M | 9 | 8 | 4.2 | 4 | 4.1 | 4.1 | 2.1 |
| M | 11 | 9 | 3.9 | 3.6 | 3.6 | 3.7 | 4.4 |
| M | 11 | 10 | 1.6 | 1.5 | 1.5 | 1.5 | 2.4 |
| F | 14 | 11 | 4.8 | 4.3 | 4.6 | 4.5 | 5.1 |
| F | 7 | 12 | 3.7 | 3.8 | 3.7 | 3.7 | 1.5 |
| F | 8 | 13 | 3.5 | 3.5 | 3.9 | 3.6 | 6 |
| M | 7 | 14 | 1.8 | 2 | 2.3 | 2 | 13.4 |
| M | 5 | 15 | <0 | <0 | <0 | <0 | |
| M | 15 | 16 | 0.4 | 0.5 | 0.6 | 0.5 | 22.7 |
| M | 7 | 17 | 0.8 | 0.7 | 0.6 | 0.7 | 9.4 |
| F | 8 | 18 | 4.3 | 4.6 | 4.5 | 4.5 | 3.5 |
| M | 5 | 19 | 5.8 | 5.6 | 5.5 | 5.6 | 2.5 |
| F | 14 | 20 | 5.1 | 5.5 | 5.4 | 5.3 | 4.3 |

Fig. 2B

METHOD FOR DIAGNOSING HEMANGIOSARCOMA IN CANINE USING DETECTION OF THYMIDINE KINASE ACTIVITY

CROSS-REFERENCE TO RELATED APPLICATIONS

The application is a continuation of patent application Ser. No. 12/260,885, filed on Oct. 29, 2008, now issued as U.S. Pat. No. 8,097,432, which in turn claims the filing-date priority of Provisional Application No. 60/983,359, filed Oct. 29, 2007, the specification of which is incorporated herein in its entirety.

BACKGROUND

1. Field of the Invention

The instant disclosure relates to method, apparatus and kit for detecting presence of cancer in certain mammals. More specifically, the disclosure relates to a method and apparatus for detecting hemangiosarcoma in canines and felines.

2. Description of Related Art

Nearly half of all dogs over the age of ten die from cancer. Conventional data indicate that the sum total for canine and feline cancer-related claims in the year 2005 was just shy of 20,000. This incident rate of newly uncovered cancer is consistent with other data.

Cancers are malignant neoplasms (growth) that occur when cell-dividing brake mechanisms (the genes that keep growth in check) go awry. Causes of these gene malfunctions may be inherited or acquired. Some breeds of dog seem particularly predisposed to develop certain types of cancer. For example, studies have shown that the English Setter, Chihuahua, Miniature Poodle and Afghan Hound have a predisposition for invasive mammary gland cancers. Boxers, American Staffordshire Terriers, Chinese Shar-Pei and Boston Terriers have a predisposition to mast cell (deep skin cell) cancers. Bernese Mountain dogs are prone to malignant histocytosis, which is a cancer of the white blood cells. Unspayed female dogs (and those spayed late in life) are more susceptible to mammary gland cancers and un-neutered male dogs (especially those with retained testicle) are at risk for testicular cancer. Malignancies are generally diseases of older dogs.

Mixed breed dogs are not immune to the development of cancer; they can suffer from malignant skin tumors if they inherit a faulty brake gene from one parent. Acquired cancers arise when the cell mechanisms are disrupted by a virus (although rare in dogs), by irradiation (skin cancers on dogs with short coats and pale skin exposed to excessive sunlight), or by an accumulation of toxic chemicals, either from failure of a cell to dispose of its waste byproducts or from natural or manmade chemicals in the environment. Body type is also implicated in the development of some types of cancer. Large and giant dogs have a higher risk of the bone cancer osteosarcoma that is associated with stress on weight-bearing limbs and dogs with dark skin are susceptible to melanomas.

Statistical data show that the most common cancers in dogs are lymphoma (a cancer affecting the lymph node system), skin tumors and osteogenic sarcoma (bone cancer). The data also suggest that cats similarly suffer from lymphoma and skin tumors.

Hemangiosarcoma ("HSA") is a malignant and rapidly growing cancer. HSA is difficult to detect. HSA is a tumor derived from blood vessels, and thus the tumor is filled with blood. A frequent cause of death from HSA is the rupturing of the tumor, causing the patient to rapidly hemorrhage to death. HSA in humans is commonly associated with toxic exposure to thorium dioxide (thorotrast), vinyl chloride and arsenic. The causes of HSA in dogs are largely unknown.

HSA is somewhat common on dogs, and more so in certain breeds of dogs such as German Shepherds and Golden Retrievers. HSA also occurs in cats, though it is rare. Dogs with HSA rarely show clinical signs until the tumor has become very large and has metastasized. Typically, clinical signs are due to hypovolaemia after the tumor ruptures, causing severe bleeding. Owners of the affected dogs often discover that the dog has HSA only after the animal has collapsed.

The HSA tumor often appears on the spleen, right heart base or liver. USA is the most common tumor of the heart and it occurs in the right atrium, where it can cause right-heart failure, arrhythmias, pericardial effusion and cardiac tamponade. HSA of the spleen or liver is the most common tumor to cause hemorrhage in the abdomen.

The success of treatment to cure 15" cancer lies in early detection of the disease. However, early detection of HSA is one of the most challenging aspects of the disease. This is primarily because HSA most commonly develops internally, where it is not easily noticed and examined. In many instances, malignant tumors arising in the organs of body will eventually cause symptoms directly related to the location of the tumor. A wait-and-see method to diagnose HSA is inappropriate since by the time the cancer is large enough to detect, it has already reached an advanced stage and is unlikely to respond favorably to treatment.

There are currently no commercially viable screening mechanisms for detecting HSA in dogs. Most dogs present with HSA as emergencies and major decisions about treatment must be made without a definitive diagnosis. A screening test that would allow the detection of HSA would be very valuable in the planning of treatment and earlier detection of the disease. Thus, there is a need for a method, apparatus and kit for early detection of HSA.

SUMMARY

In one embodiment, the disclosure relates to a method for detecting Hemangiosarcoma (HSA) in canines, the method comprising: obtaining a quantity of blood from the subject canine; separating the quantity of blood into a serum portion and a non-serum portion; contacting the serum portion of the blood with a detector to detect presence of an amount of Thymidine Kinase (TK); detecting the level of TK activity in serum and determining whether TK is present in amounts of about 8 units/liter or greater.

In another embodiment, the disclosure relates to a system for detecting HSA in canines, comprising: a centrifuge for separating a serum portion of the subject canine blood from a non-serum portion; a detector for detecting presence of an amount of Thymidine Kinase (TK); and an indicator for quantifying a level of TK presence in an amount of about 8 units/liter or greater.

BRIEF DESCRIPTION OF THE DRAWINGS

These and other embodiments of the disclosure will be discussed with reference to the following exemplary and non-limiting illustrations, in which like elements are numbered similarly, and where:

FIG. 1 shows the result of the HSA cancer study in Table 1;
FIGS. 2A and 2B show data from the control samples;

DETAILED DESCRIPTION

Figure 3:
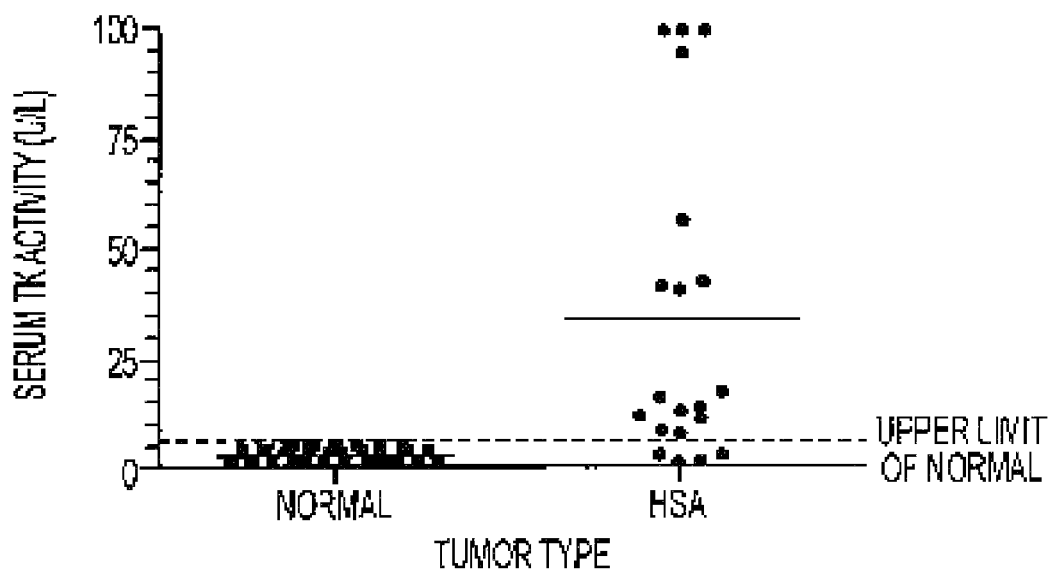
FIG. 3 shows scatter plot depicting the TK activity values for 18 dogs with HSA (red) and 33 age-matched healthy control dogs (black)

Thymidine Kinase ("TK") is a salvage enzyme and TK is only present in anticipation of cell division. Accordingly, TK will only be set free to the circulation from cells undergoing divisions. The enzyme is not set free from cells undergoing normal division where the cells have a special mechanism to degrade the proteins no longer needed after the cell division. In normal subjects the amount of TK in serum or plasma is therefore very low. Tumor cells release the TK enzyme to the circulation, probably in connection with the disruption of dead or dying tumor cells. The TK level in serum therefore serves as a measure of malignant proliferation, indirectly as a measure of the aggressiveness of the tumor.

In one embodiment of the invention, serum TK is used as a potential tumor marker for detecting hemangiosarcoma in veterinary patients. In another embodiment, the disclosure relates to identifying a threshold for detecting the HSA from the presence of TK isoenzymes.

Previous studies have demonstrated TK's potential utility as a marker for detecting lymphoma in dogs. However, despite overwhelming need and interest, no marker has been available for detecting HSA in dogs. The following sample studies were conducted to provide viability of the proposed method.

Eighteen serum samples from dogs presented to an emergency clinic with hemoabdomen, and subsequently demonstrated to have HSA of the liver or spleen by histopathology, were evaluated for TK activity. Serum samples previously stored at −80° C. were assayed; Sera from aged-matched clinically normal dogs comprised a control population (n=30). Comparisons between groups were made using 1- and 2-tailed unpaired T-tests as appropriate.

For each sample, approximately 600 microliter serum was provided. Each sample was labeled with a database code for blind testing and patient identification. The control group included dogs with no history of illness. From each dog approximately 3 ml whole blood from a peripheral vein was extracted into a red-top tube. For each sample serum were separated from the cells within 60 minutes and the samples were then frozen immediately.

The samples were then defrosted and analyzed using the LIAISON@ Thymidine Kinase Assay Procedure (Registered to DiaSorin S.p.a of Italy). The analysis included reacting each sample with a substrate having 3'-derivative of thymidine in the presence of a phosphate donor and a buffer system. The phosphate donor was a nucleoside triphosphate suitable to transfer a phosphate group to a substrate such as adenosine triphosphate (ATP) or cytidine triphosphate (CTP). The buffer system included 10-100 mM HEPES or Tris with pH ranging from 6.8-8.0, 1-30 mM DTE, 0.2-8 mM ATP and $MgCl_2$ at a concentration of at least twice the concentration of ATP. The substrate contained 3'-derivative of thymidine. A more detailed discussion of the assay can be found in Application No. 2006/0035295 A1 to Oehrvik et al., the specification of which is incorporated herein in entirety by reference for background information.

The LIAISON® TK assay procedure included a two-step, competitive chemiluminescence immunoassay (CLIA) for quantitative determination of TK in serum and EDTA plasma. The assay utilizes an initial enzymatic reaction in which TK in the sample converts AZT (3'-azido-3'-deoxythymidine) to AZTMP (3'-azido-3'-deoxythymidine monophosphate). This is followed by a competitive immunoassay for the quantitative determination of AZTMP. The amount of AZT converted to AZTMP is a measure of the amount of TK present in the sample.

In the experiment, 50 microliter of sample was incubated with 100 microliter of Assay Buffer 1, 20 microliter of Assay Buffer 2, and 20 microliter of paramagnetic particles coated with anti-AZTMP polyclonal antibody. Rabbit anti-goat IgG, then anti-AZTMP goat polyclonal is coated to the solid phase.

The sample incubated for about 40 minutes and then 100 microliter of tracer, an AZTMP analogue conjugated to an isoluminol derivative is added. During the first incubation, AZTMP binds to the solid phase. In the second incubation, the tracer conjugate competes for binding with the AZTMP in the solution. After a 20 minute incubation, the unbound material is removed with a wash cycle. The starter reagents are then added and a flash chemiluminescent reaction is initiated. The light signal is measured by a photomultiplier as relative light units (RLU) and is proportional to the concentration of TK present in calibrators, controls, or samples.

Statistical comparisons between groups were made using 1- and 2-tailed unpaired T-tests as appropriate.

The raw data from the described experiment are provided in Table 1 of FIG. 1. The results of the control study is tabulated at Tables 2A and 2B of FIG. 2. More specifically, the control group consisted of normal dogs of matching age and sex distribution to the study group and are tabulated in Table 2 and Table 3 and shown graphically in FIGS. 2 and 3. The control group represents dogs unaffected with hemangiosarcoma or other apparent disease and provides the statistical basis for calculating the reference interval.

TK activity in normal canine serum ranged from 0-5.6 U/L (mean 2.8 U/L). An upper limit of normal (mean+2 SD) was established at 6.16 U/L. TK activity was significantly higher than control (P<0.0001) in dogs with HSA (mean+/−SD=34.2+1-36.5, see FIGS. 1 and 2). In about 80% of dogs with HSA, serum activity was above the normal range. Using the available data, the described assay appears to have an approximately 80% sensitivity for detecting canine visceral HSA.

Figure 4:
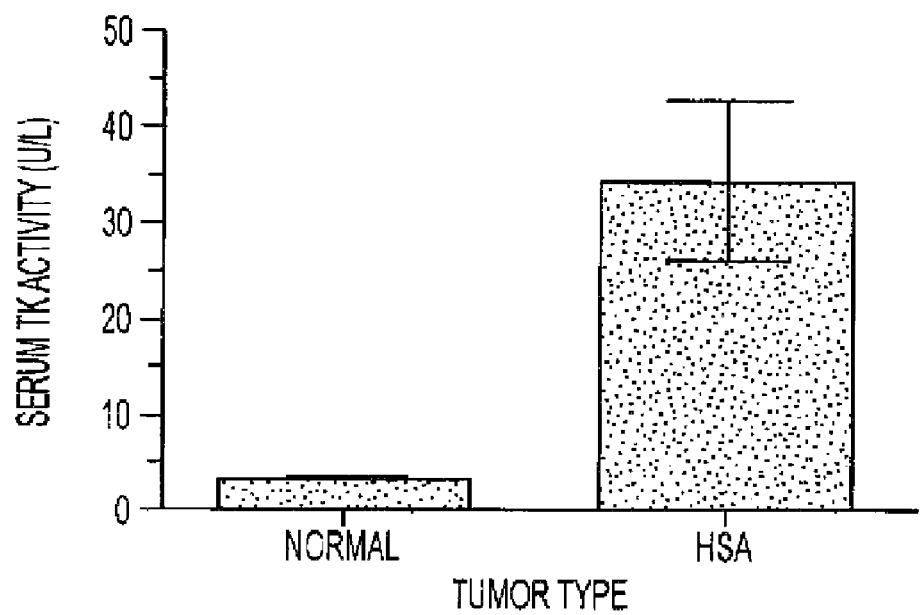
FIG. 4 shows mean (+1–SEM) TK activity values in 18 dogs with HSA and 33 age-matched healthy control dogs.

FIG. 3 shows scatter plot depicting the TK activity values for 18 dogs with HSA (red) and 33 age-matched healthy control dogs (black). FIG. 4 shows mean (+/−SEM) TK activity values in 18 dogs with HSA and 33 age-matched healthy control dogs.

The experiment's results lead to the following conclusions: (1) TK is significantly increased in dogs with some types of cancer, specifically HSA; (2) TK may be useful in staging and monitoring disease in veterinary patients with HSA.

While the principles of the disclosure have been illustrated in relation to the exemplary embodiments shown herein, the principles of the disclosure are not limited thereto and include any modification, variation or permutation thereof.

What is claimed is:

1. A method for detecting visceral Hemangiosarcoma in canine subjects comprising:
   obtaining a blood sample from a canine subject;
   obtaining a serum portion from said blood sample;
   providing a substrate having a 3'-derivative of thymidine;
   providing a phosphate donor for releasing a phosphate radical;
   incubating said serum portion in a solution comprising said substrate and said phosphate donor to cause a phosphorylation reaction resulting in the transfer of said phosphate radical from said phosphate donor to said substrate, producing a phosphorylated substrate;

measuring a concentration of said phosphorylated substrate;

determining a level of Thymidine kinase activity based on said concentration of said phosphorylated substrate; and determining said canine subject has Hemangiosarcoma with approximately 80% sensitivity if said level of activity of Thymidine kinase is higher than about 8 units per liter.

2. The method of claim 1 wherein said providing said substrate further comprises providing 3'-azido3'-deoxythymidine.

3. The method of claim 2 wherein the step of measuring further comprises measuring the concentration of 3'-azido3'-deoxythymidine mono-phosphate.

4. The method of claim 1 wherein said step of providing said phosphate donor further comprises providing adenosine triphosphate.

5. The method of claim 1 wherein said step of providing said phosphate donor further comprises providing cytidine tri-phosphate.

6. The method of claim 1, wherein said step of determining said level of Thymidine kinase activity further comprises comparing said concentration of said phosphorylated substrate to a concentration of thymidine kinase in calibrators.

7. The method of claim 1, wherein said step of determining further comprises determining said canine subject as an unlikely carrier of Hemangiosarcoma carriers if said level of TK enzymatic activity is below about 8 units per liter.

* * * * *